United States Patent [19]
de Zbikowski

[11] Patent Number: 4,524,765
[45] Date of Patent: Jun. 25, 1985

[54] FUNCTIONAL ATTACHMENT SYSTEM FOR OSTEOSYNTHESIS BY MEANS OF COMPRESSION PLATES

[76] Inventor: Juan L. de Zbikowski, Virgen de la Antigua, 10-1º, Sevilla, Spain

[21] Appl. No.: 448,329

[22] Filed: Dec. 9, 1982

[30] Foreign Application Priority Data

Dec. 9, 1981 [ES] Spain .................. 507.800

[51] Int. Cl.³ .............................. A61F 5/04
[52] U.S. Cl. ................. 128/92 D; 128/92 B
[58] Field of Search ............ 128/92 D, 92 R, 92 B

[56] References Cited

U.S. PATENT DOCUMENTS

| | | | |
|---|---|---|---|
| 2,486,303 | 10/1949 | Longfellow | 128/92 D |
| 3,659,595 | 5/1972 | Haboush | 128/92 D |
| 4,119,092 | 10/1978 | Gil | 128/92 D |
| 4,219,015 | 8/1980 | Steinemann | 128/92 D |

FOREIGN PATENT DOCUMENTS 1949923 4/1971 Fed. Rep. of Germany .... 128/92 B

OTHER PUBLICATIONS

Zimmer–USA, Warsaw, Ind. 46580, catalog, p. B143, Rev. 1, dated 6/27/80.

*Primary Examiner*—C. Fred Rosenbaum
*Assistant Examiner*—C. W. Shedd
*Attorney, Agent, or Firm*—Wender Murase & White

[57] ABSTRACT

An improved functional attachment system for osteosynthesis by means of compression plates. The plates have straight or angled construction and a major axis for placement approximately parallel to the major axis of a bone. The plate defines holes in the areas of both ends; the holes are elongated in a direction approximately parallel to the plate's major axis and are adapted for receipt and passage of anchoring screws for attachment to a bone. Once the compression plate is attached to a fractured bone by means of anchoring screws passing through the holes, the screws can slide the length of the elongated holes such that muscular contraction will be converted into a compression at the bone fracture.

5 Claims, 5 Drawing Figures

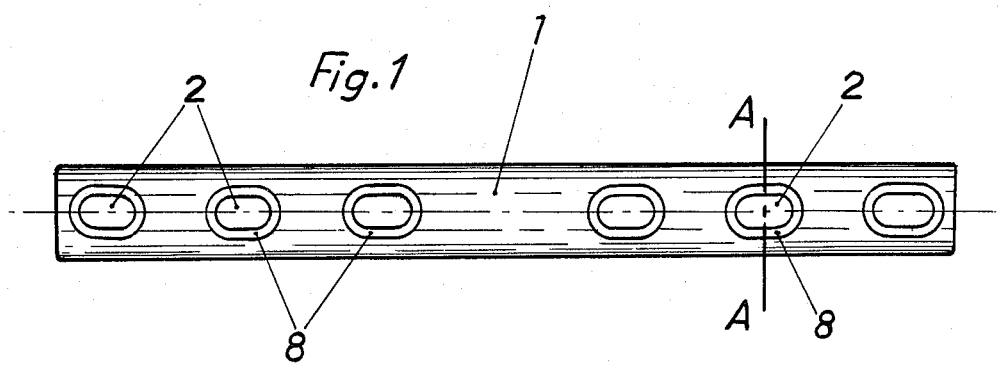
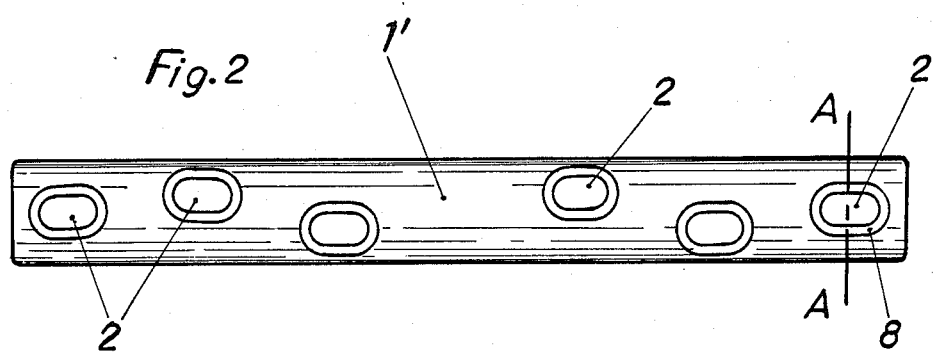
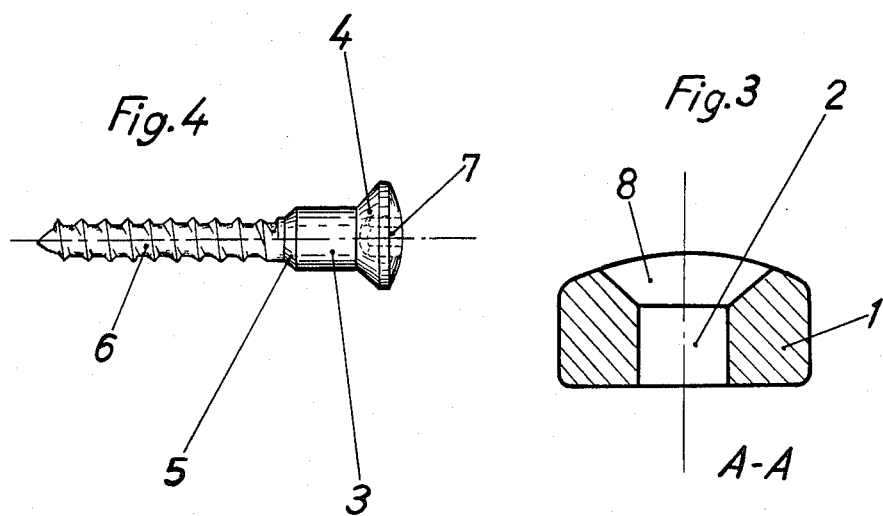

FUNCTIONAL ATTACHMENT SYSTEM FOR OSTEOSYNTHESIS BY MEANS OF COMPRESSION PLATES

BACKGROUND OF THE INVENTION

1. Field of the Invention

The invention relates to improvements introduced into the functional attachment system for osteosynthesis, by means of compression plates.

2. Description of the Prior Art

The use in osteosynthesis of various types of plates is known for exerting a strong pressure on the two parts of the bone on both sides of the fracture. One of said types of plates makes use of auxiliary systems consisting of a turnbuckle, which is joined by means of screws to one of the parts of the bone in such a way that this turnbuckle forces the bone into which the plate is screwed closer to the other part of the bone so that they press against one another, in addition to which said plate is also joined with screws to the other part of the bone, at which time the turnbuckle is removed.

Another known system for functional attachment for osteosynthesis, created in fact by the inventor of these improvements, is based on the mechanical or biomechanical principle of providing the compression plates with a special device that slides parallel to the major axis of the bone in such a way that the muscular contraction is converted into an impacting or compression at the focus of the fracture between the fragments equal in magnitude and opposite to said contraction. A similar effect is produced by the action of "muscle tone," which is a state of minor permanent contraction, or by the action or gravity and load. The principle is thus carried out whenever mechanical devices are used in internal osteosynthesis that neutralize or tend to neutralize all angular, lateral or rotational movements, with movement in the direction of the bone axis remaining free. Hence this is osetosynthesis in which the "bridge," with a solid osseous anchor, is formed of one or two parts sliding together.

All current osteosynthetic systems are based on achieving absolute rest for the focus, including under compression at the line or focus, in order to increase stability by means of endless screw systems, internal tension created on plates, etc.; but in all these techniques compression is virtually invariable and its magnitude entirely empirical.

The compression plates used in the aforementioned systems all have major drawbacks, among which may be cited the need for a meticulous and complicated application as well as the need for precise machining. Despite all this satisfactory results that would justify such requirements have not been achieved.

SUMMARY OF THE INVENTION

In applying the improvements under the invention to the already known system of functional attachment for osteosynthesis by means of compression plates, the principle continues to be utilized that the magnitude of the compression is variable in relation to function, which, from least to greatest importance are muscle tone (rest); muscular contraction (movement); weight (bipedal standing); and dynamic load (walking; weight multiplied by acceleration). All these magnitudes of compression are physiological and variable.

Compression plates for fastening in osteosynthesis, provided with the improvements according to the invention, maintain the basic property of allowing movement in the primary direction of the plate and of the bone axis; because of their excellent effects, these may be called biocompression plates. In order to achieve this effectively and simply, the improvements provide for the formation of a plate, either straight or angled, and of various lengths and shapes, having the original characteristic of bearing in the areas of both ends some elongated holes, with the inner longitudinal sides straight and parallel and with the ends curved, having a bevel or notches around the upper opening to form a countersink or seat for the head of the respective screw to be inserted into the hole, while the rest of the hole has vertical walls perpendicular to the base, constituting a guidehole for the movements of the smooth neck or shaft of the screw, for purposes of biocompression. The screws also have been constructed in a special way consisting of calculating the thread pitch of its spirals so that the separation between the spirals coincides with the resistance limit of the ball-and-socket joint of the bone, there being between the base of the screw head, the lower part of which must have the shape of a truncated cone, and the start of the thread a smooth cylindrical portion or neck, at the lower end of which its circular edge must have a specially created bevel to adapt it to the opening of the hole in the bone, with the beneficial effect that it prevents breaking or damage to same. There will be an assortment of screws with smooth cylindrical area or neck of various lengths to be used in attaching a plate, screws with various neck lengths so that the holding of the plate is adapted to the curves and iiregularities of the bone surface.

Due to the various shapes and sizes of the various bones and the economy and diversity of types of fracture, the range of sizes for the biocompression plates will be very broad in order to cover these needs; they may thus vary in terms of weight, thickness, length, width, number of holes for screws and arrangement of same, aligned in quincunxes or placed irregularly; they may also be planar or of different curvatures for adaptation in all cases to the curves of the fractured bones.

The drawings show two examples of realization of biocompression plates for the improved functional attachment system for osetosynthesis according to the invention; these drawings must be given a broad and general interpretation without being subject to constructive details, since they may vary according to the particular cases of application.

BRIEF DESCRIPTION OF THE DRAWINGS

Said drawings show in the following figures:

FIG. 1. Bottom of a biocompression plate with its holes aligned in a straight arrangement.

FIG. 2. Bottom of a biocompression plate, with its holes arranged in quincunxes.

FIG. 3. Transversal cross-section along A-B of FIGS. 1 and 2.

FIG. 4. Lateral view of one of the screws.

DESCRIPTION OF THE PREFERRED EMBODIMENTS

Figure 5:
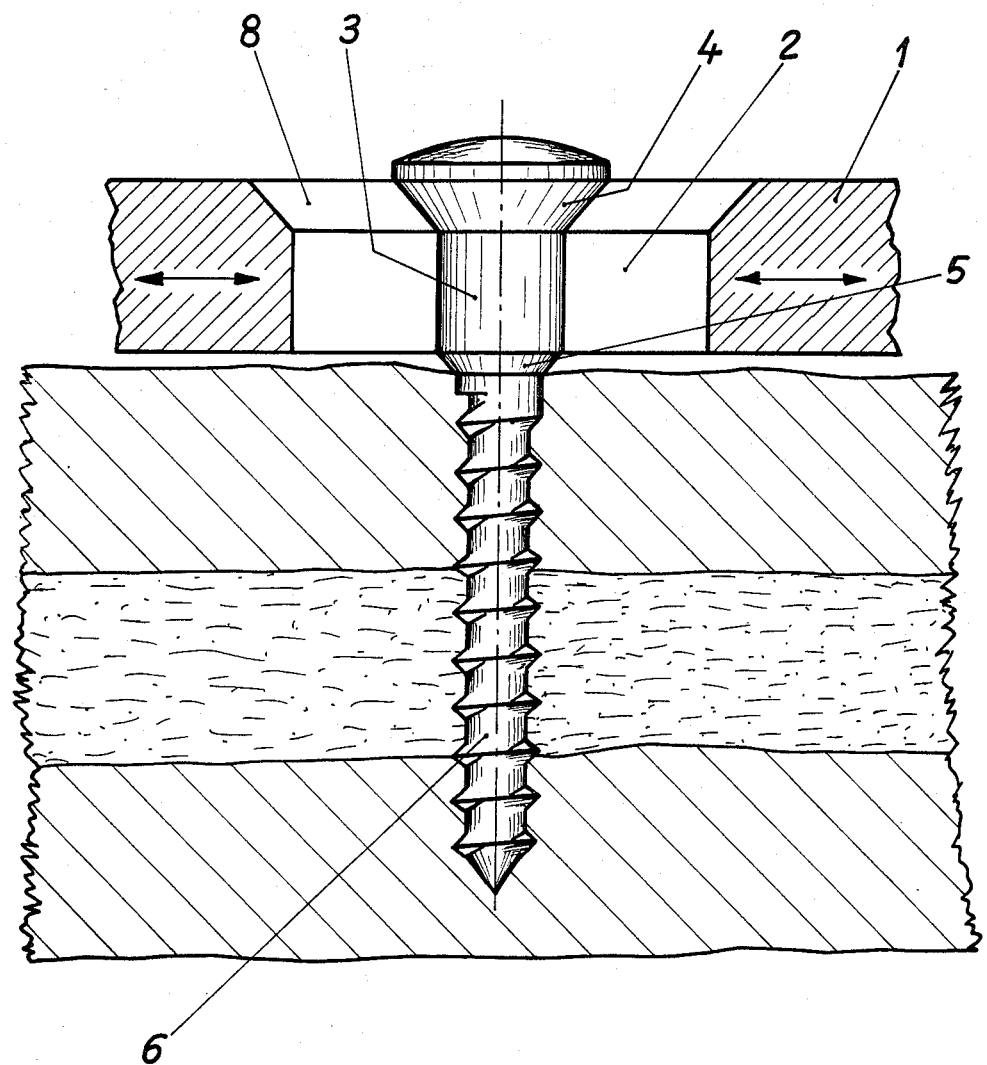
FIG. 5 shows a screw constructed in accordance with the teachings of the present invention screwed into a bone with the head and neck portions thereof slidably captured by a biocompression plate.

The biocompression plates shown in FIGS. 1, 2 and 3 consist of a metal plate, indicated by -1-, -1'-, with its upper surface or face curved convexly in a transversal direction (FIG. 3), the plates of which bear in the areas of both ends a group of elongated holes -2- which, as can be seen in the figure, are aligned in a straight line, although they may also be arranged in quincunxes as in FIG. 2; the number of holes may vary, although in these examples three are shown in each area of the ends.

Each elongated hole 2 has its upper opening with a bevel or countersink 8, while the rest of the hole has its walls vertical and perpendicular to the base forming an elongated guide.

The screw, designated by 7, has its head in the shape of a spherical cap, and on the lower part an inverted, truncated cone shape -4- with the incline of its surfaces corresponding to the same degree of incline of the bevel or countersink -8- in which they are to sit and be able to slide. Next, the body or shaft of the screw -7- has a smooth, cylindrical portion -3-, there being an assortment of screws with this portion of various lengths, with the important particularlity for this case of application that the lower end of said cylindrical area -3- ends in a truncated-cone-shaped bevel or chamfer -5- that can be adapted to the hole in the bone to prevent damage or breaking. With regard to the threading -6-, its pitch or separation of spirals has been calculated to coincide with the break limit of the bone.

I claim:

1. A functional attachment system for biocompressive osteosynthesis for connecting bone portions on either side of a fracture site of a fractured bone comprising:
    (a) a plate having a major axis adapted to be oriented generally parallel to a major axis of the fractured bone, said plate having end portions adapted to be positioned on either side of said fracture site respectively, each of said end portions having holes elongated in a direction generally parallel to the major axis of said plate; and
    (b) means attached to the bone portions for capturing said plate end portions with respect to the bone portions through said elongated holes, so as to allow relative displacement between each bone portion and said plate generally paallel to said plate major axis in response to biocompressive forces.

2. The osteosynthesis system according to claim 1 wherein:
    (a) the plate has a lower face for placement against the bone portions and an upper face opposite the lower face;
    (b) the elongated holes have inner longitudinal sides approximately parallel to the major axis of said plate, said longitudinal sides being straight and parallel with respect to each other, and curved ends joining the longitudinal sides;
    (c) a beveled countersink formed in said upper face at each of said elongated holes; and
    (d) each of said elongated holes forms a guidehole for guiding movement of said attachment means.

3. A functional attachment system for biocompressive osteosynthesis for connecting bone portions on either side of a fracture site of a fractured bone comprising:
    (a) a plate having a major axis adapted to be oriented generally parallel to a major axis of the fractured bone, said plate having end portions adapted to be positioned on either side of said fracture site respectively, each of said end portions having holes elongated in a direction generally parallel to the major axis of said plate; and
    (b) means attached to the bone portions for capturing said plate end portions with respect to the bone portions through said elongated holes, so as to allow relative displacement between each bone portion and said plate generally parallel to said plate major axis so that once said plate is captured on the fractured bone, said means for attachment can slide the length of the elongated holes, and muscular contraction is converted into biocompressive force at the focus of the fracture.

4. The osteosynthesis system according to claim 3 wherein:
    (a) the plate has a lower face for placement against the bone portions and an upper face opposite the lower face;
    (b) the elongated holes have inner longitudinal sides approximately parallel to the major axis of said plate, said longitudinal sides being straight and parallel with respect to each other, and curved ends joing the longitudinal sides;
    (c) a beveled countersink formed in said upper face at each of said elongated holes; and
    (d) each of said elongated holes forms a guidehole for guiding movement of said attachment means.

5. The osteosynthesis system according to any one of claims 1–4, wherein said attachment means comprises:
    (a) screws with threads having a pitch constructed at a previously-calculated distance so that the separation between threads coincides with the maximum resistance to breaking of the bone to which it is attached;
    (b) a screw head having a base, and a lower part having the shape of a truncated cone;
    (c) a smooth cylindrical neck between said screw head base and said threads, said neck having a diameter less than that of the screw head and being adapted for slidable guided movement in said elongated holes, and a neck edge abutting the threads, said neck edge having a bevel for adaptation to the opening of a hole made in a bone in order to prevent breaking or damage of the bone hole and for prevention of further threading of said screw into the bone.

* * * * *